United States Patent [19]

Price

[11] Patent Number: 5,542,843
[45] Date of Patent: Aug. 6, 1996

[54] ROTATABLY DRIVEN AUTOCLAVABLE LIGATION INSTRUMENT

[76] Inventor: Michael T. Price, 3870 Lake Haughey Rd., Maple Plain, Minn. 55359

[21] Appl. No.: 408,213

[22] Filed: Mar. 22, 1995

[51] Int. Cl.⁶ .................... A61C 3/00; B21F 7/00
[52] U.S. Cl. ............... 433/4; 433/159; 606/148; 140/119; 140/121
[58] Field of Search ............ 433/4, 159; 606/103, 606/139, 144, 148, 206, 208; 140/118, 119, 121

[56] References Cited

U.S. PATENT DOCUMENTS

| | | | |
|---|---|---|---|
| 1,740,392 | 12/1929 | Donaldson | 140/119 |
| 2,394,807 | 2/1946 | Robinson | 140/119 |
| 2,737,983 | 3/1956 | Pray | 140/119 |
| 3,092,152 | 6/1963 | Neff | 140/119 |
| 4,392,494 | 7/1983 | Ashby | 433/4 |
| 4,842,025 | 6/1989 | Box et al. | 140/119 |
| 5,211,209 | 5/1993 | Geibel et al. | 140/121 |

FOREIGN PATENT DOCUMENTS 3032236  4/1982  Germany ............... 606/103

OTHER PUBLICATIONS

Ortho–Ply catalog, p. 21.
Parker, Quick Coupling Division, p. A8.
Photograph (marked Exhibit A) of airline industry tool.

*Primary Examiner*—Cary E. O'Connor
*Attorney, Agent, or Firm*—Schroeder & Siegfried, P.A.

[57] ABSTRACT

An autoclavable ligation instrument for use in dental or medical applications which includes a ligature gripping tool having a pair of jaws with handle members connected thereto, and a drive mechanism for causing rotational movement of the gripping tool for consequent twisting of opposite ends of a ligature being gripped thereby. The drive mechanism includes a spring biased helically shaped drive shaft which is engaged by a drive follower nut that is connected to the gripping tool, such that activation of the drive mechanism causes the drive follower nut, and consequently the gripping tool, to rotate about the helically shaped drive shaft. The gripping tool includes a releasable locking mechanism for locking the jaws of the gripping tool in their closed position, and the gripping tool and drive mechanism are disassemblable and constructed of an autoclavable material to facilitate sterilization thereof.

27 Claims, 6 Drawing Sheets

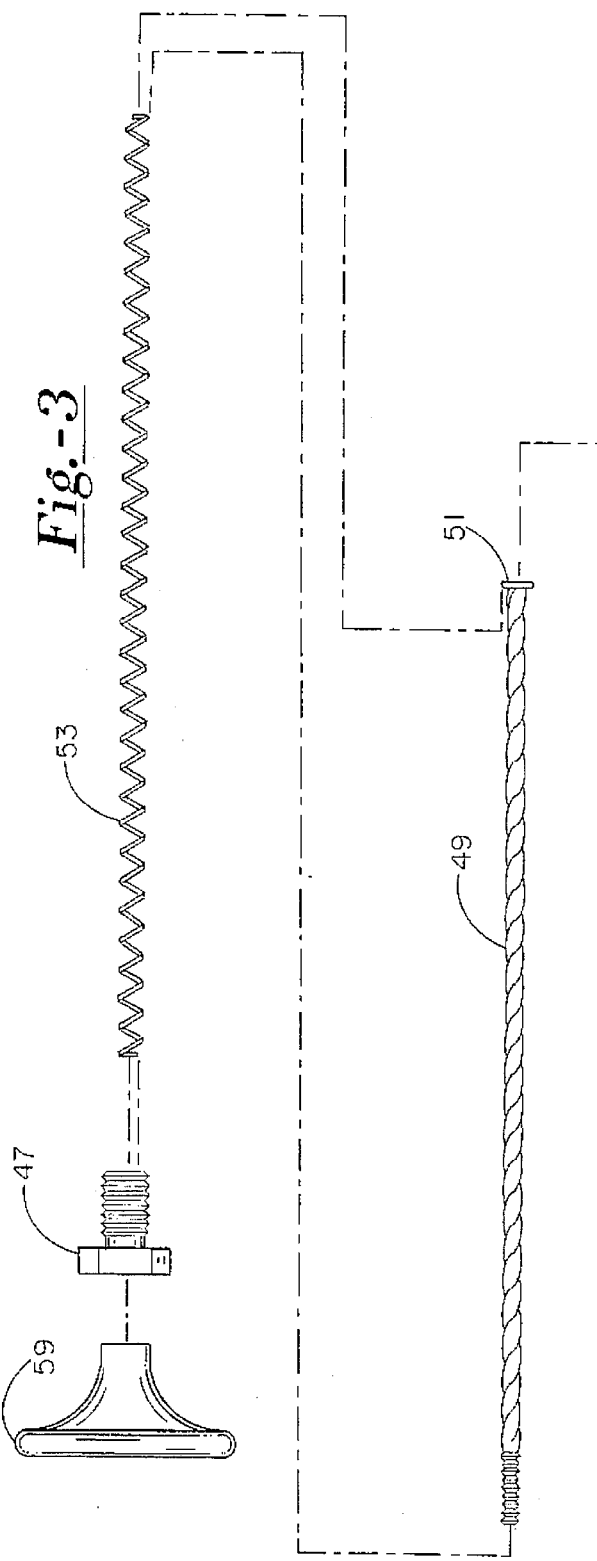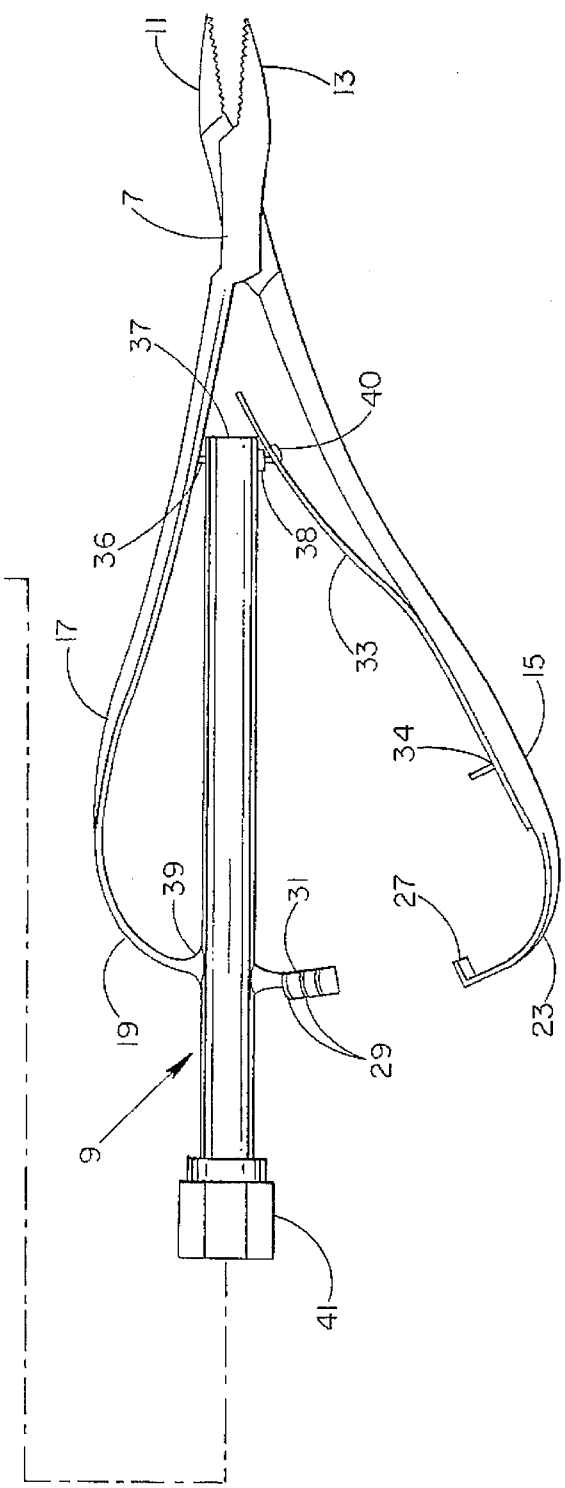
Fig.-3

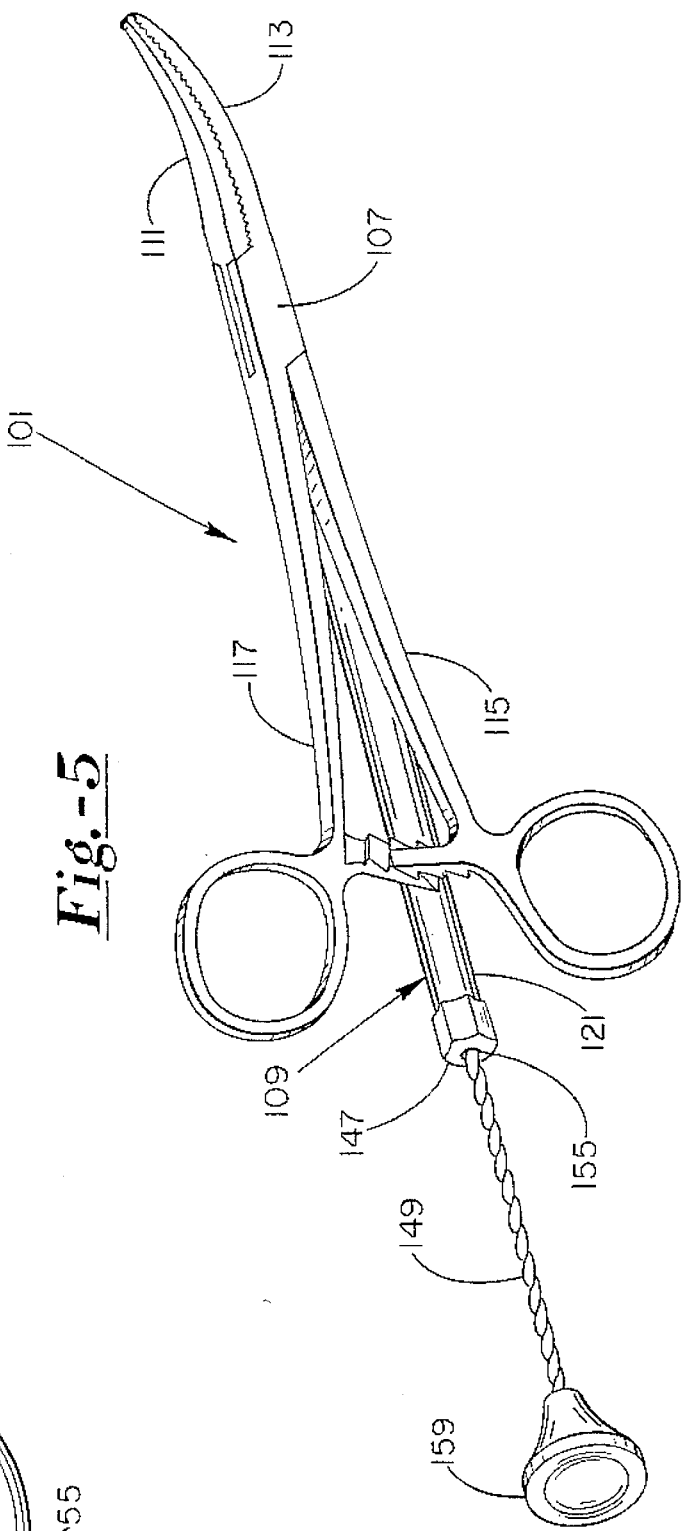
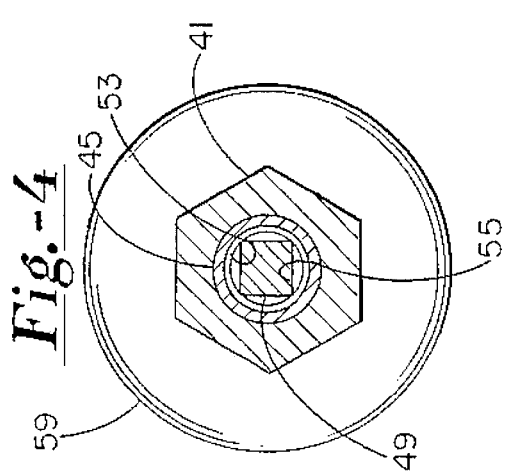

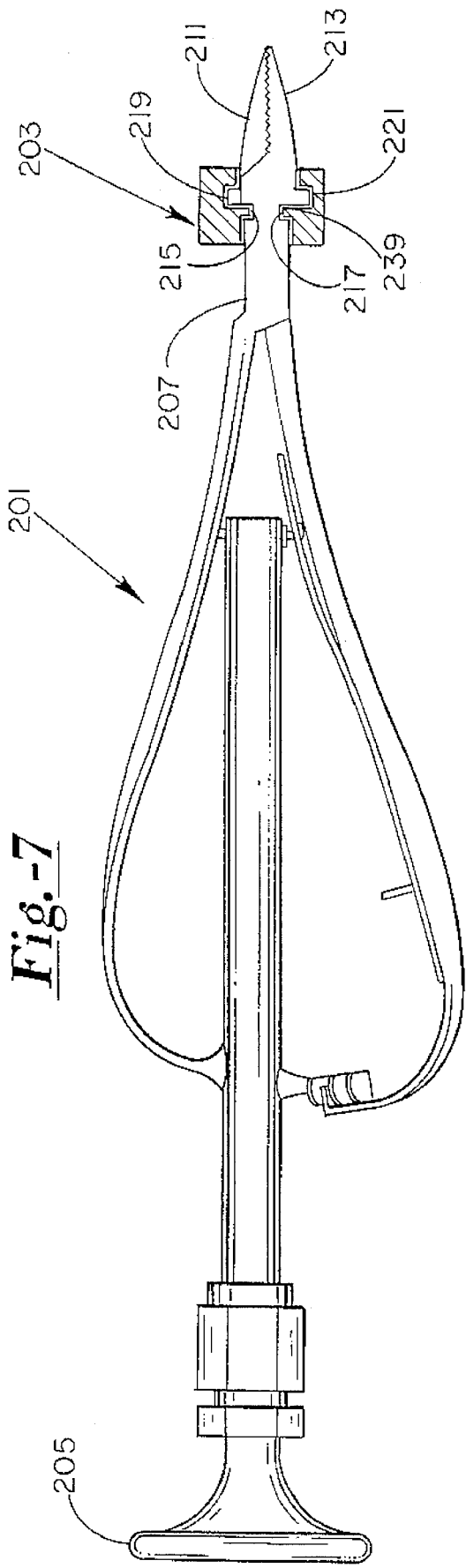
Fig. 7
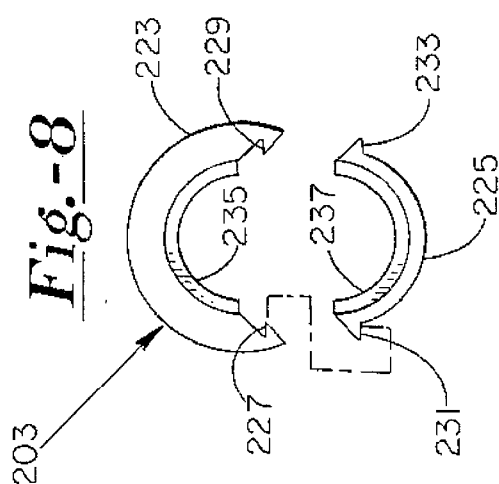
Fig. 8
Fig. 9

ROTATABLY DRIVEN AUTOCLAVABLE LIGATION INSTRUMENT

BACKGROUND OF THE INVENTION

The present invention is related generally to instruments or tools used within the dental and/or medical professions, and more specifically related to a ligation instrument used for gripping and tying various ligatures used in such professions, which is constructed to be rotatably driven and readily disassemblable for sterilization through autoclaving thereof.

The use and tying of ligatures is commonplace in the dental and medical profession during orthodontic and surgical procedures, as well as other medical procedures requiring the setting of bones, etc. Conventional ligating instruments for such use generally comprise a miniature pliers which is constructed of autoclavable stainless steel. The instrument typically includes a pair of relatively small jaws capable of gripping the ends of a fine wire or other ligature in locking relation so as to allow the dentist or doctor, or assistant thereof, to manually twist the tool by hand, so as to wind the wire or ligature for tying the same.

Such conventional tools, which require manual hand manipulation are time consuming to use, and can cause significant fatigue to the user. Moreover, continued use of such tools may eventually lead to more serious health related problems associated with carpal tunnel syndrome, due to the frequent and repeated rotative twisting movement which the user must make in order to twist the ligature for tying the same. Not only is the use of such conventional tools extremely time consuming, their repeated use can lead to significant health problems.

Such conventional tools are cumbersome to manipulate by hand, particularly in areas of small compass, which oftentimes results in poor quality ligature ties that are rough or jagged, and looser than desirable. Such poor quality ties can cause chafing of a person's mouth, and in more delicate operations, can be a significant safety and durability concern.

The problems associated with conventional ligation instruments are long standing, and have become even more significant in recent years through the heightened awareness of the health problems associated with carpal tunnel syndrome. As long as dentists have been practicing orthodontics, and bones have been set with the tying of ligatures, such conventional ligation tools, and the significant problems associated therewith, have been present.

As can be seen from the above, there is significant need for a ligation tool which is easier to use in delicate operations, and which will reduce or eliminate the time, fatigue and carpal tunnel health problems associated through repeated use thereof. It is, therefore, the object of the present invention to provide an improved ligation instrument which produces a higher quality ligature tie, and eliminates the need for the user of such a tool to continually and repeatedly impart a twisting motion thereto through repetitive movement of their wrist and fingers. By elimination of the need for such movement, the fatigue and likelihood of eventual problems with carpal tunnel syndrome will be significantly reduced, as well as the time necessary for completing the tying of such a ligature.

In addition to the above, it is the object of the present invention to provide such an improved ligation instrument which is constructed completely of an autoclavable material, and which is readily disassemblable to facilitate ease and effectiveness of sterilization through autoclaving.

BRIEF SUMMARY OF THE INVENTION

The present invention constitutes a relatively lightweight autoclavable ligation instrument which is comprised generally of a ligature gripping tool to which a rotational drive mechanism is connected for imparting rotational movement to the gripping tool as needed.

The gripping tool includes a pair of movable jaws which are pivotally connected to one another for movement between an open position and a closed position, where such jaws pinch together for grasping of a ligature, wire or other tying member. Each of the respective jaws includes a handle member extending rearwardly thereof which is designed for comfortable handling to cause the jaws to move between their open and closed position. At least one of the handle members is spring biased so as to cause the jaws to rest in a normally open position. Squeezing the respective handles of the jaws together causes the jaws to move to their closed position.

Connected between the handles of the gripping tool is a locking mechanism, which allows the handle members to be lockably engaged upon closure of the jaws. The ligature to be tied may be lockably pinched between the jaws of the instrument without the need for continued maintenance of pressure against the handles by the user. The locking mechanism is designed to be readily releasable, however, for ease of use of the gripping tool over continuous and repeated applications.

The rotational drive mechanism which is connected to the gripping tool is comprised preferably of an elongated tubular member which telescopically receives therein an elongated helically shaped drive shaft that is used to impart the desired rotational movement to the gripping tool to which the tubular member is attached. The elongated tubular member is preferably connected to one of the handle members and positioned such that its longitudinal axis is disposed along a line which extends between the jaws of the gripping tool when closed.

Rigidly connected to the rear terminal end of the tubular member is a drive follower nut which has an opening extending therethrough for passage of the helically shaped drive shaft. The opening-defining portions of the drive follower are constructed such that the drive follower will engage the drive shaft in contouring relation, and be caused to rotate thereabout upon applying a longitudinal pulling force to the helically shaped drive shaft. To facilitate the capability of applying such a longitudinal force to the drive shaft, the rear terminal end of the drive shaft has an enlarged knob fixedly connected thereto which may be easily grasped.

Contained within the tubular member, and telescopically disposed over the drive shaft, is an elongated spring. The spring causes the drive shaft to be biased toward a normal resting position, whereby the rear knob of the drive shaft rests in abutting relation to the drive follower that is connected to the tubular member. The drive shaft biasing spring is disposed between the drive follower that is connected to the rear terminal end of the tubular member, and a stop that is formed at the forward terminal end of the drive shaft. Upon pulling the drive shaft rearwardly, the gripping tool rotates and the spring compresses. Upon release of the drive shaft, the force of the compressed spring will cause the drive shaft to return to its normal resting position.

It is particularly desirable for all components of the gripping tool, and locking and drive mechanism, to be constructed of a rigid autoclavable material, as such tools must be capable of withstanding repeated sterilization through autoclaving thereof. Therefore, in order to accommodate and make the entire instrument autoclavable, the drive mechanism is constructed so as to be disassemblable for autoclaving of its components. To accomplish this, the drive follower nut is threadably connected to the outer tubular member of the drive mechanism, thereby allowing disassembly thereof and complete removal of the drive shaft and biasing spring from the interior of the tubular member. By disassembling the drive mechanism of the ligation instrument, each of the components thereof may be effectively sterilized through autoclaving.

In use, such a relatively lightweight autoclavable ligation instrument may be used to grip a ligature and twist the ends thereof for tying purposes. For instance, an orthodontist commonly uses such an instrument for tying wires which are used to tighten an individual's braces on their teeth. With a conventional ligation tool, it is necessary to grip each ligature with the gripping tool, and manually, by hand, rotate the gripping tool until proper tying of the ligature is attained. This requires a repeated rotative motion of the wrist and fingers which is time consuming, tiresome, and can eventually lead to more significant health problems caused by the onset of carpal tunnel syndrome.

With the present invention, the ligature is grasped and locked between the jaws by engaging the locking mechanism between the handles of the gripping tool. By applying a longitudinal pulling force to the rear knob of the drive shaft, the drive follower will engage the helically shaped drive shaft, thereby causing the tubular member, and consequently the gripping tool, to readily spin as the drive follower advances along the helical path of the drive shaft. Therefore, by applying a pulling force to the drive shaft, the needed tying of the ligature is accomplished.

For more delicate operations, such as the resetting of broken bones, it may not be desirable to apply a pulling force on the ligature. In such cases, a grip bearing member may be connected to the gripping tool which allows the user to offset the longitudinal pulling force imparted to the drive shaft, and consequently the ligature, while allowing the gripping tool to continue to rotate to cause the twisting and tying of the ligature.

As is apparent, use of my improved ligation instrument requires no twisting or rotative motion of the user's wrist and fingers, thereby eliminating the fatigue and potential problems associated with conventional ligation instruments, and substantially reducing the amount of time necessary to perform the tying operation which is to be conducted. Both the quality and durability of the resulting ties are markedly improved as a result of the continuous substantially symmetrical rotative force which is applied to the ligatures. Moreover, because my improved ligation instrument is compact in size, lightweight, and constructed of readily disassemblable and autoclavable components, it is ideal for use in many delicate dental and medical procedures for which conventional ligation instruments are unsuitable.

BRIEF DESCRIPTION OF THE DRAWINGS

These and other objects and advantages of the invention will more fully appear from the following description, made in connection with the accompanying drawings, wherein like reference characters refer to the same or similar parts throughout the several views, and in which:

FIG. 3 is an exploded view of my improved ROTATABLY DRIVEN AUTOCLAVABLE LIGATION INSTRUMENT, showing the various components which comprise the instrument and drive mechanism therefor;

FIG. 4 is a sectional view, taken along lines 4—4 in FIG. 2, of the rear portion of the drive mechanism showing the engagement between the drive follower and helically shaped drive shaft;

FIG. 5 is a perspective view of an alternative embodiment of my improved ROTATABLY DRIVEN AUTOCLAVABLE LIGATION INSTRUMENT, showing the drive mechanism mounted in such manner that its longitudinal axis extends between the jaws of the gripping tool when closed;

FIG. 7 is a side elevational view of a front portion of another alternative embodiment of my improved ROTATABLY DRIVEN AUTOCLAVABLE LIGATION INSTRUMENT, showing in vertical section a grip bearing means which may be attached thereto for offsetting applied longitudinal forces to the drive mechanism of such instrument; and FIG. 8 is a front elevational exploded view of the grip bearing means depicted in FIG. 7, showing the manner of construction thereof.

FIG. 9 is a front elevational view of the grip bearing means depicted in FIG. 7, showing the manner in which the components thereof lockably engage.

DETAILED DESCRIPTION OF THE INVENTION

Figure 1:
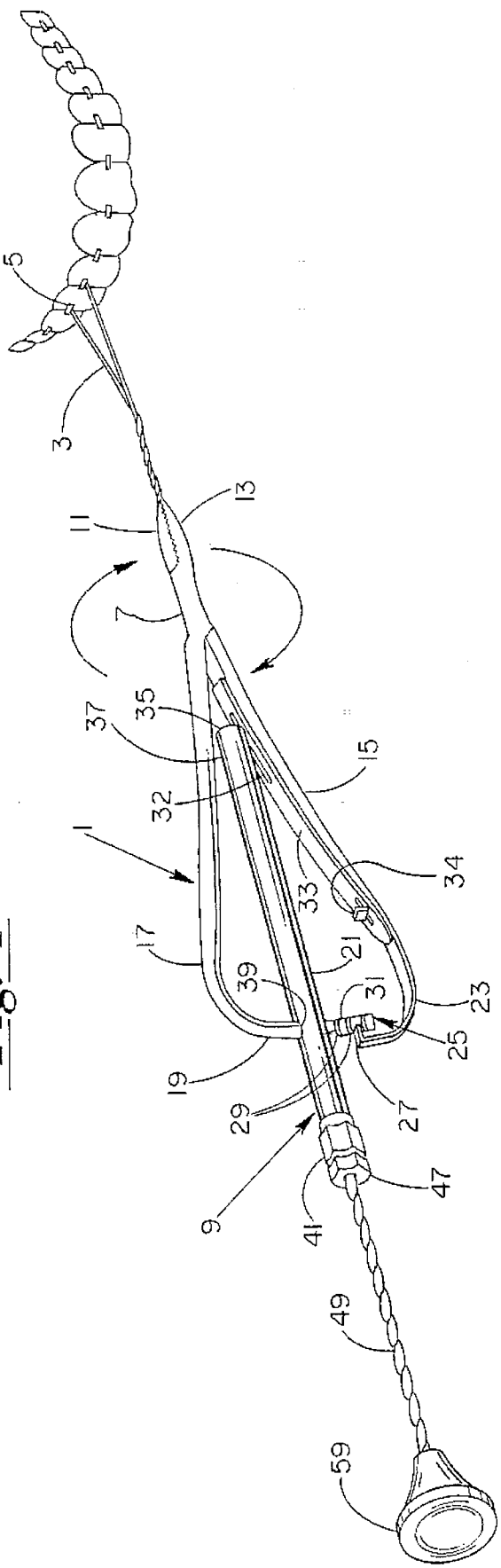
FIG. 1 is a perspective view of my improved ROTATABLY DRIVEN AUTOCLAVABLE LIGATION INSTRUMENT, showing the operation thereof to tie an orthodontic ligature wire.

As shown in FIG. 1, my improved, lightweight autoclavable ligation instrument 1 is well suited for applications in orthodontics, wherein the tightening of wires 3 to a person's braces 5 may be readily accomplished without the need for repeated manual rotation of the instrument. Although application of my improved ligation instrument 1 is shown in connection with an orthodontic application, it is readily apparent that many conceivable applications exist for the tying of ligatures in the medical, veterinarian and dental industries, in which my improved ligation instrument 1 will be of substantial benefit.

As shown in FIG. 1, my improved, lightweight autoclavable ligation instrument 1 is comprised generally of a relatively small ligature gripping tool 7 to which a rotational drive mechanism 9 is connected for imparting rotational movement to the gripping tool as needed for tying purposes. As shown best in FIG. 2, the ligature gripping tool 7 includes a pair of movable jaws 11 and 13 which are pivotally connected to one another for movement between an open and closed position. Cantilevered from jaws 11 and 13, and extending rearwardly thereof, are respective handle members 15 and 17. Handle members 15 and 17 diverge outwardly and rearwardly from the pivotal connection between jaws 11 and 13 in a smooth, contouring manner, which facilitates ease of gripping the same in the palm of a person's hand.

The rear end portion 19 of handle member 17 curves inwardly toward handle member 15, and terminates in a fixed connection 39 to the outer tubular housing 21 of rotational drive mechanism 9. The forward end portion 37 of tubular member 21 is also connected to handle member 17 at point 35 to provide additional stability to drive mechanism 9.

Similarly, the rear end portion 23 of handle member 15 curves inwardly toward handle member 17 and drive mechanism 9. The rear terminal end of handle member 15 forms a latch 27 which is constructed to lockably engage in a readily releasable manner one of a plurality of shoulders 29 formed in an associated catch means 31 of locking mechanism 25. Catch means 31 is fixedly connected to outer tubular member 21 of drive mechanism 9, and extends outwardly therefrom in a direction toward handle member 15.

Figure 2:
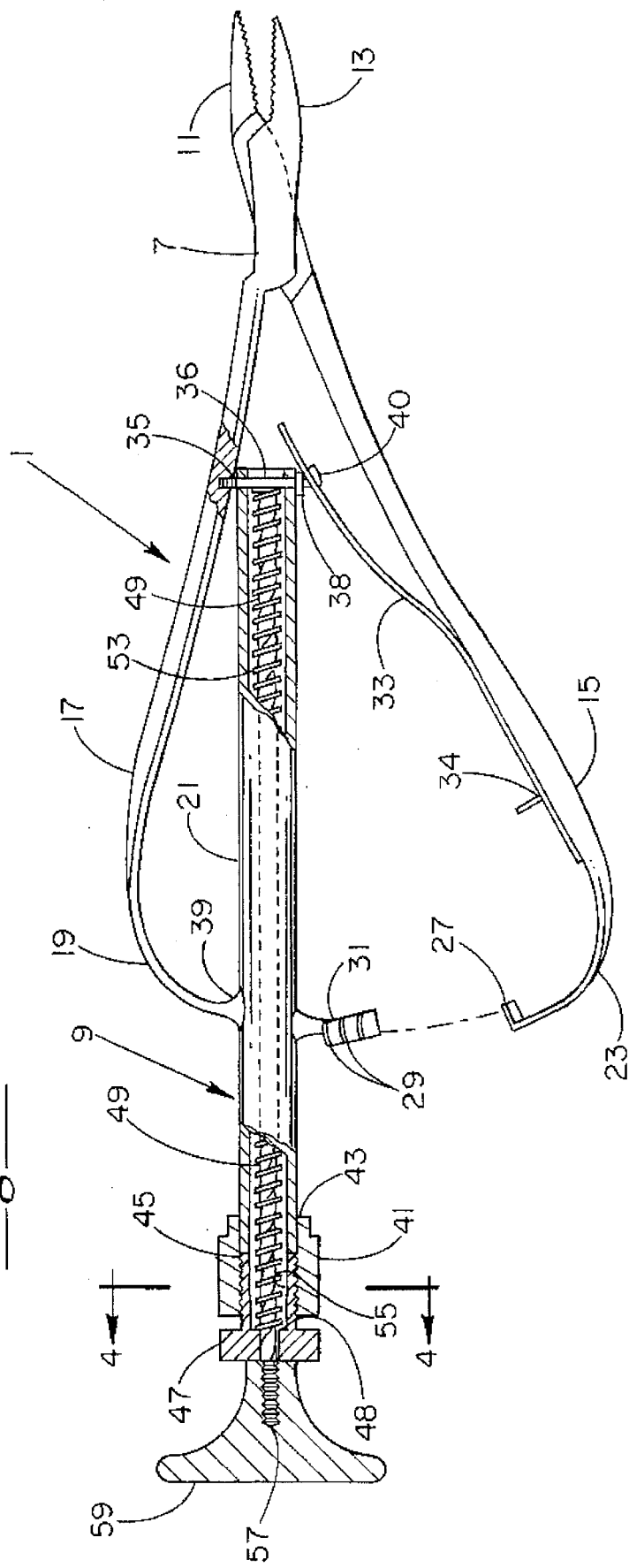
FIG. 2 is a side elevational view of my improved ROTATABLY DRIVEN AUTOCLAVABLE LIGATION INSTRUMENT, with portions of the drive mechanism broken away to show the internal construction thereof.
Figure 6:
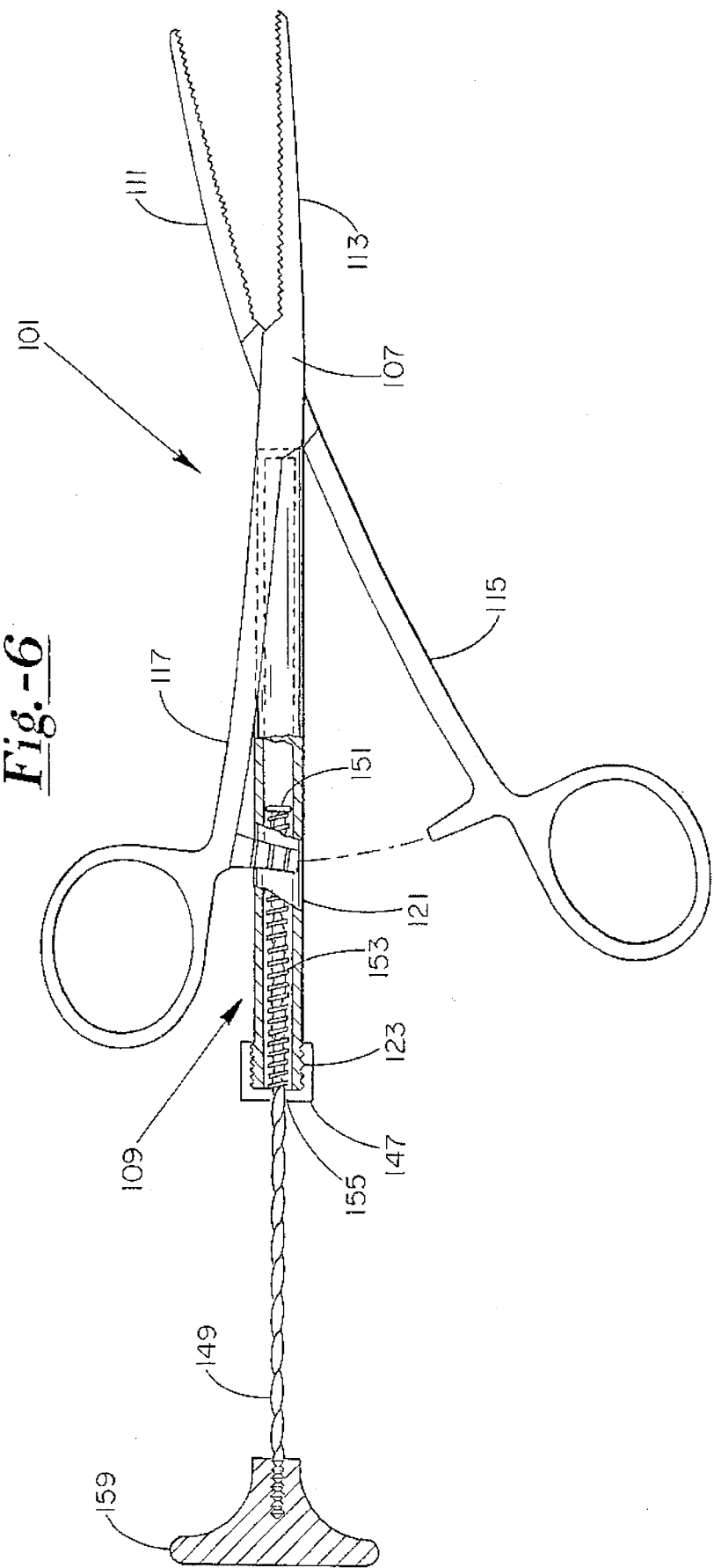
FIG. 6 is a side elevational view of the alternative ligation instrument disclosed in FIG. 5, with portions of the drive mechanism thereof broken away to show the alternative construction thereof.

As is readily apparent from FIG. 2, the gripping force of jaws 11 and 13 may be adjusted as needed for a given application. As handle members 15 and 17 are compressed together to cause closure of jaws 11 and 13, latch 27 will engage one of the shoulders 29 of catch 31. Increased compression of handles 15 and 17 toward one another will cause latch 27 to advance and catch on a shoulder 29 closer to drive mechanism 9, thereby retaining jaws 11 and 13 at a tighter grip. Depending on the gauge of the wire or ligature being tied, the gripping force of jaws 11 and 13 may be adjusted accordingly. Thus, my improved ligation instrument 1 is suitable for use in applications involving the use of heavier gauge wires and ligatures, as well as extremely fine wires and ligatures.

Applying additional compression to handle members 15 and 17 will cause latch member 27 to advance beyond the innermost shoulder 29 adjacent to drive mechanism 9, thereby causing latch 27 to release from the catch means 31, so as to allow jaws 11 and 13 to move to an open position.

In order to facilitate opening of jaws 11 and 13, it is noted that such jaws are biased toward their open position by means of spring 33 which is attached to handle member 15 at connection 34. Spring 33 curves outwardly away from handle member 15 toward handle member 17, and is designed to bear against the forward end portion 37 of tubular member 21 of drive mechanism 9. As handle member 15 and 17 are compressed together, spring 33 is forced downwardly by tubular member 21 toward handle member 15, thereby causing spring 33 to create a continuous resistive force against compression of handle members 15 and 17. Such resistive force generated by spring 33 causes jaw members 11 and 13 to move to a normally open position, as shown in FIG. 2, upon release of compression from handle members 15 and 17.

As shown best in FIGS. 2 and 3, and as stated previously, drive mechanism 9 includes an outer elongated tubular member 21, which is secured to handle member 17 at point 35 adjacent its forward end 37, and at point 39 intermediate its forward end 37 and rear end thereof. At point 39, tubular member 21 is preferably welded or otherwise suitably connected to handle member 17 in fixed relation. At point 35, tubular member 21 is secured to handle member 17 via an elongated pin 36 with head 38, which extends through an opening in end 37 of tubular member 21, and is secured by suitable means to handle member 17. In the preferred construction, as shown in FIG. 2, pin 36 threads into an opening in handle member 17, causing head 38 to bear against tubular member 21 to hold the same securely in place. The curved extension 40 of pin 36 extends through an elongated central slot 32 (see FIG. 1) in spring 33, and functions to prevent spring 33 from slipping off and disengaging the end portion 37 of tubular member 21.

As shown best in FIG. 1, tubular member 21 of drive mechanism 9 is disposed such that its longitudinal axis extends between jaws 11 and 13 when closed. Consequently, rotational drive movement imparted to the ligature gripping tool 7 will be substantially symmetrical about the ligature 3 being held by jaws 11 and 13. It is further noted that, in the embodiment shown in FIG. 1, tubular member 21 of drive mechanism 9 is disposed within a plane defined by the movement of handle members 15 and 17.

Disposed at the rear end of tubular member 21, and connected thereto through welding or other suitable securing means, is drive nut 41. Drive nut 41 has an opening 43 which receives tubular member 21 therein for rigid connection thereto. The opposite end of drive nut 41 includes a threaded bore 45 which is designed to threadingly receive drive follower 47 therein.

As can be seen best from FIGS. 2 and 3, an elongated helically shaped drive shaft 49 having a forward end stop 51 is received telescopically within outer tubular member 21. Telescoping over drive shaft 49 and bearing against forward end stop 51 is an elongated biasing spring 53. Biasing spring 53 extends within a central longitudinal opening 55 in drive follower 47, and bears against and is held within tubular member 21 by the base shoulder 48 of the head of drive follower 47. Opening 55 continues through drive follower 47 to accommodate drive shaft 49, which extends therethrough and into opening 57 of knob 59. Drive shaft 49 is preferably threadably connected to knob 59 for disassembly thereof, but may also be secured thereto by any other suitable connection means.

The central opening 55 extending through drive follower 47 is greater in diameter throughout its threaded portion to accommodate spring 53. As shown in FIG. 4, however, opening 55 is preferably generally square-shaped through its outermost head portion, such that it forms a contouring wear surface which engages the helical contour of drive shaft 49, thereby causing the drive follower 47, and consequently drive mechanism 9 and ligature gripping tool 7, to rotatably follow the helical contour of drive shaft 49 as it is pulled longitudinally through opening 55 in drive follower 47. Depending on the direction of the helical contour of drive shaft 49, clockwise or counterclockwise, the gripping tool 7 may rotate in either direction. Drive shaft 49 can be designed either way, depending on the preference of the user.

Biasing spring 53 rests within tubular member 21 in its relaxed state when drive shaft 49 is positioned most inwardly within tubular member 21. Upon pulling on knob 59, thereby causing drive shaft 49 to move outwardly through opening 55 in drive follower 47, biasing spring 53 compresses between end stop 51 and drive follower 47. By so doing, biasing spring 53 creates a restorative force which bears against stop 51 such that, upon release of knob 59 by the user, drive shaft 49 will be caused to return to its initial resting position within tubular member 21.

Components of the ligature gripping tool 7 and drive mechanism 9 are preferably constructed of a high quality rigid autoclavable material, such as a high grade stainless steel with a mirror finish. This will ensure enhanced wear characteristics of the instrument during sterilization thereof.

Of course, it is conceivable that other autoclavable materials may be used in the construction of such instruments where custom designing for specific applications is necessary.

It is noted that it is preferable for the drive mechanism to be capable of being easily disassembled for better sterilization of the individual components. To disassemble the drive mechanism 9, a person need only unscrew the drive follower 47 from the drive nut 41, thereby enabling the drive shaft 49 and telescoping biasing spring 53 to be removed from within tubular member 21. By so doing, each component of the drive mechanism 9 may be placed within an autoclave for proper sterilization thereof. Moreover, by being readily disassemblable, my improved ligation instrument 1 is designed for easy repair and installation of replacements parts, when necessary.

As can be seen best in FIG. 1, operation of my improved autoclavable ligature instrument eliminates the time consuming, painstaking process of manually twisting, by hand, the conventional ligation instruments used for tightening wires or other ligatures in orthodontic and other dental and medical procedures. By effectively eliminating the need for repeated manual twisting of such tying members 3, my new ligation instrument 1 also reduces the fatigue and potential health related problems related to the carpal tunnel syndrome, which has become so prevalent in recent years in operations involving procedures such as that shown in FIG. 1.

In use, as can be seen in FIG. 1, the ligature gripping tool 7, with its jaws 11 and 13, grip a typical ligature or tying member 3 by compressing handle members 15 and 17 toward one another until latch mechanism 27 engages an appropriate shoulder 29 on catch 31. Having locked the ends of the tying member 3 within the jaws of ligature gripping tool 7, the user may release his or her grip from handle members 15 and 17, and hold the instrument 1 from knob 59 of a drive mechanism 9. By pulling knob 59 longitudinally away from drive follower 47, drive follower 47, and consequently drive mechanism 9 and ligature gripping tool 7, will spin in the direction of the arrows shown in FIG. 1, so as to rotatably follow the helical path defined by drive shaft 49. Therefore, by longitudinally pulling drive shaft 49 through drive follower 47, the gripping tool 7 will cause the wire or tying member 3 to be smoothly wound and tightly tied. No manual twisting motion is necessary, as drive mechanism 9 causes the necessary rotative movement.

Because my improved ligation instrument 1 applies a substantially continuous symmetrical rotative force to the ligature 3 being tied, the quality of the resultant tie is much better than that which can be achieved through manual hand tying. The resulting ties are smoother, smaller in diameter, and tighter. In orthodontic applications, such higher quality ties result in less food becoming trapped in poor quality ties, and less chafing of the inside of the wearer's mouth.

Because it is no longer necessary to maintain a grip on handle members 15 and 17 in order to cause rotation of gripping tool 7, as it is with a conventional ligation instrument, my improved ligation instrument 1 may be used in extremely tight areas of small compass where hand manipulation of a conventional ligator would be difficult. The smooth, uniform resulting tie formed by my improved ligation instrument 1 enhances both the durability and safety of such ligature ties. Of course, if desired by the user, the drive mechanism 9 of my improved ligation instrument may be readily disassembled for use of the instrument in a conventional manner through hand manipulation.

An alternative embodiment of my improved autoclavable ligation instrument is shown in FIG. 5, and is designated as numeral 101. The ligation instrument 101 includes a modified ligature gripping tool 107 which has somewhat longer curved jaws 111 and 113. In this embodiment, the ligation instrument 101 functions in the same manner as that described previously, but the drive mechanism 109 is secured to handle member 117 on its outer surface such that it is disposed in a plane parallel with, but not within, the plane defined by the movement of handle member 117 and 115. Drive mechanism 109 is mounted to handle member 117 such that the longitudinal axis of drive mechanism 109 extends between the curved jaws 111 and 113, when closed, at a point adjacent the forward end thereof. Thus, gripping a ligature between jaws 111 and 113 at the point of intersection with the longitudinal axis of drive mechanism 109 will facilitate substantially symmetrical rotation of gripping tool 107 about the ligature being held by jaws 111 and 113.

Drive mechanism 109 is constructed and functions in much the same manner as drive mechanism 9, disclosed previously, with the exception that the rear end of tubular member 121 has external threads 123, and drive follower 147 is comprised of a threaded cap which screws onto the rear end of tubular member 121. The opening 155 in drive follower 147 is again constructed to form a contouring wear surface which engages the helical shape of the drive shaft 149 extending therethrough, thereby causing the gripping tool 107 to rotate about drive shaft 149 as shaft 149 is pulled through drive follower 147.

Drive mechanism 109 is also readily disassemblable for purposes of facilitating adequate sterilization of the components of the instrument through autoclaving. For such purposes, each of the components of the drive mechanism 109 and ligature gripping tool 107 are preferably constructed of a high quality rigid autoclavable material, such as a high quality stainless steel.

Similar to the, previously described ligation instrument 1, operation of ligation instrument 101 is effected by pulling on knob 159, thereby causing the helical drive shaft 149 to travel through drive follower 147. As the opening 155 through drive follower 147 is constructed to contour the cross section of drive shaft 149, similar to that shown in FIG. 4, the drive follower 147 and gripping tool 107 connected thereto will rotatably follow the helical pattern of drive shaft 149, thereby causing the instrument to rotate about the longitudinal axis thereof. Any ligature or other tying means being held by gripping tool 107 will be smoothly twisted so as to rapidly tighten and tie the same.

It is noted that, similar to ligation instrument 1, the biasing spring 153 in ligation instrument 101 is compressed upon pulling drive shaft 149 outwardly from within tube 121. Upon completion of pulling drive shaft 149 outwardly the user may hold gripping tool 107 stationary while releasing knob 159. The force of the compressed biasing spring 153 at such time will bear against end stop 151 of drive shaft 149, thereby causing drive shaft 149 and biasing spring 153 to return to their initial resting positions within tubular member 121.

The ligation instruments shown in FIGS. 1 and 5 represent only two designs which may be used in the dental and medical industries. As numerous designs of conventional ligators and hemostats are commercially available, it is certainly conceivable that other designs may be readily adaptable to support a drive mechanism such as that disclosed herein. It is the structural design and location of the gripping jaws which will ultimately determine how the drive mechanism should be connected to the instrument, so that the longitudinal axis of the drive mechanism will extend between the closed jaws of the tool to cause smooth and symmetrical twisting of a ligature.

It is evident that each of the embodiments of my improved ligation instrument shown in FIGS. 1 and 5 require a longitudinal pulling force to be applied to the drive shaft of the instrument in order to cause the same to rotate for tying of a ligature. Such pulling force on the drive shaft is necessarily transferred into the associated ligature which is being tied thereby. In certain more delicate operations, however, such as the resetting of bone fractures, it may not be desirable to generate such a pulling force on a ligature which is being tied. Under such circumstances, as shown in FIG. 7, an alternative ligation instrument 201 may be used, which has been modified for use in connection with a grip bearing means 203, that functions to offset the pulling pressure normally exhibited upon the ligature when the instrument is in use. As can be seen in FIG. 7, the forward end portion of the gripping tool 207 adjacent jaws 211 and 213 is formed with upper and lower radially inwardly protruding grooves 215 and 217. Such inwardly protruding grooves 215 and 217 are positioned adjacent to, but rearward of, upper and lower radially outwardly protruding retaining shoulders 219 and 221.

As can be seen best in FIGS. 8 and 9, grip bearing 203 is comprised of a pair of readily releasable, lockably engaging arcuately shaped half-shell members 223 and 225 which may be constructed of a rigid autoclavable material, similar to the ligation instrument 201, or alternatively, may be constructed of a material which is readily disposable after use thereof, such as a moldable polyolefin. The semi-circular shell members 223 and 225 are preferably constructed with suitable locking means to secure the members together during use thereof. For illustration purposes, as shown in FIGS. 8 and 9, semi-circular half-shell members 223 and 225 are constructed with opposing locking shoulders 227, 229 and 231, 233, respectively, which lockably engage to form grip bearing 203. Semi-circular half-shell members 223 and 225 include radially inwardly protruding bearing flanges 235 and 237 which form an inner annular bearing ring 239 when half-shell members 223 and 225 are interconnected.

As shown best in FIG. 7, to use grip bearing 203, semi-circular half-shell members 223 and 225 are positioned around the front end portion of gripping tool 207 and locked together, such that the inner annular bearing ring 239 of grip bearing 203 seats within the upper and lower grooves 215 and 217 formed in the forward portion of gripping tool 207. With the ligature held in place between jaws 211 and 213, grip bearing 203 may be held firmly in place while pulling on the knob 205 which is connected to the drive shaft. Under such circumstances, the inner annular bearing flange 239 will bear against retaining shoulders 219 and 221 to offset the pulling pressure exerted upon the drive shaft. Gripping tool 207 will still be allowed to rotate within grip bearing 203, which is loosely fitted thereon, thereby allowing the ligature being held by gripping tool 207 to be rapidly and smoothly tied without applying a longitudinal pulling force thereto. Upon completion of the tying of the ligature, half-shell members 223 and 225 may be unlocked and disengaged from gripping tool 207, and reused as needed, or disposed of, in such case that the grip bearing 203 is constructed of a disposable material.

As is apparent, there are substantial advantages to using my improved autoclavable ligation instrument over conventional tools of this type. The manual hand operation, which is extremely time consuming, and causes significant fatigue and eventual more significant problems with carpal tunnel syndrome, are substantially eliminated. Through application of one or more relatively light, longitudinal pulling forces to the helically shaped drive shaft of my improved ligation instrument, a wire ligature or other tying member being held by the gripping tool will automatically and rapidly be twisted, tightened and tied. The resulting ties are smoother, tighter, and more durable and uniform, due to the continuous symmetrical rotation of the ligation instrument during use thereof. Moreover, the adjustability of the gripping strength and its ability to function in areas of small compass makes my improved ligation instrument well suited for delicate operations requiring fine or small wire ligatures. Because my improved ligation instrument is compact in size, lightweight, and constructed of readily disassemblable autoclavable components, it is ideal for many applications in the dental and medical fields, and is a significant improvement over conventional hand manipulated tools of this type.

It will, of course, be understood that various changes may be made in the form, details, arrangement and proportions of the parts without departing from the scope of the invention which comprises the matter shown and described herein and set forth in the appended claims.

I claim:

1. An autoclavable ligation instrument for use in dental or medical applications, comprising:
    a. a ligature gripping means having a pair of opposed jaws movable between open and closed positions for clamping the ligature, and a handle member connected to each of said jaws for moving said jaws between said open and closed positions;
    b. a releasable locking means connected to said ligature gripping means for releasably locking said opposing jaws in said closed position;
    c. drive mechanism connected to said ligature gripping means for imparting rotational movement to at least said jaws of said gripping means upon activation thereof; and
    d. said drive mechanism and said gripping means being constructed throughout of an autoclavable material; and
    e. said drive mechanism including a tubular member fixedly connected to said ligature gripping means with a readily disassemblable end cap, and a drive shaft extending through said end cap and into said tubular member, said end cap being monolithically formed and constituting a drive follower which engages said drive shaft in driven relation.

2. The structure defined in claim 1, wherein said drive shaft is helically shaped and said drive follower engages said drive shaft in rotatably driven relation.

3. The structure defined in claim 1, wherein said drive follower engages said drive shaft in rotatably driven relation, said drive follower being connected to said gripping means in driving relation thereto.

4. The structure defined in claim 1, wherein said jaws of said gripping means are spring biased toward said open position.

5. The structure defined in claim 1, wherein said drive shaft is elongated, having a longitudinal axis which extends between said jaws of said gripping means.

6. The structure defined in claim 5, wherein said longitudinal axis of said drive shaft extends within a plane defined by said handle members.

7. The structure defined in claim 5, wherein said longitudinal axis of said drive shaft is laterally spaced relative to a plane extending between said handle members.

8. The structure defined in claim 1, wherein said drive shaft is spring biased to return to an initial resting position after activation thereof.

9. An autoclavable ligation instrument for use in dental or medical applications, comprising:
(a) a ligature gripping tool formed of an autoclavable material throughout, said gripping tool including a pair of opposed jaws which are movable between open and closed positions, and a handle member connected to each of said jaws for facilitating movement of said jaws between said open and closed position;
(b) a readily releasable locking mechanism formed of an autoclavable material throughout and connected between said handle members of said ligature gripping tool for releasably locking said opposing jaws in said closed position;
(c) a multi-piece drive means including an elongated tubular member fixedly connected to said ligature gripping means, an end cap, and a drive shaft, all formed of an autoclavable material throughout and connected to said ligature gripping tool for facilitating rotational movement of said gripping tool about an axis extending between said jaws thereof, said end cap being formed as a one-piece unit and constituting a drive follower which engages said drive shaft in driven relation;
(d) said drive means being readily disassemblable to facilitate efficient autoclaving of said multiple pieces thereof.

10. The structure defined in claim 9, wherein said drive shaft is spring biased and helically shaped, said drive follower engaging said drive shaft in rotatably driven relation.

11. The structure defined in claim 9, wherein said drive follower engages said drive shaft in rotatably driven relation, said drive follower being connected to said gripping tool in driving relation.

12. The structure defined in claim 11, wherein said drive shaft is spring biased to return said drive shaft to an initial resting position after activation of said drive means.

13. The structure defined in claim 9, wherein said drive shaft is elongated, having a longitudinal axis which extends between said jaws of said gripping tool.

14. The structure defined in claim 1, including a grip bearing means constructed for movable engagement of said gripping tool for offsetting longitudinal forces applied to said drive shaft during activation thereof.

15. The structure defined in claim 14, wherein said grip bearing means is generally tubular with a radially inwardly protruding annular bearing flange, said grip bearing means being telescoped over a portion of said gripping tool such that said bearing flange engages said gripping tool to offset longitudinal forces applied to said gripping tool while allowing rotational movement of said gripping tool therewithin.

16. A ligation instrument for use in dental or medical applications, comprising:
(a) a ligature gripping tool having a pair of opposed jaws which are movable between open and closed positions, each of said jaws having a handle member cantilevered therefrom to facilitate movement of said jaws between said open and closed positions;
(b) a releasable locking mechanism connected to said gripping tool in such manner as to enable readily releasable locking of said jaws in said closed position;
(c) a drive mechanism having an elongated drive shaft connected to said gripping tool for facilitating rotational movement of said gripping tool about an axis extending between said pair of jaws when closed; and
(d) a grip bearing means movably connected to said gripping tool for offsetting longitudinal forces applied to said drive shaft during use thereof.

17. The structure defined in claim 16, wherein at least said gripping tool, said locking mechanism and said drive mechanism are constructed of an autoclavable material, and said drive shaft is readily disassemblable from said drive mechanism.

18. The structure defined in claim 16, wherein said drive mechanism includes a drive follower which is connected to said gripping tool in disassemblable relation, and engages said drive shaft in rotatably driven relation.

19. The structure defined in claim 18, wherein said drive shaft is helically shaped.

20. The structure defined in claim 16, wherein said drive mechanism includes a spring biasing means for said drive shaft to cause said drive shaft to return to an initial resting position after activation thereof.

21. The structure defined in claim 16, wherein the longitudinal axis of said elongated drive shaft extends within a plane defined by the movement of said handle members.

22. The structure defined in claim 16, wherein the longitudinal axis of said elongated drive shaft is disposed lateral of a plane defined by the movement of said handle members.

23. The structure defined in claim 16, wherein said jaws of said gripping tool are biased toward said open position.

24. The structure defined in claim 16, wherein said grip bearing means telescopes over a forward portion of said gripping tool and is constructed to facilitate rotational movement of said gripping tool therewithin.

25. The structure defined in claims 16 or 24, wherein said grip bearing means is constructed of a pair of semi-circular shell members which lockably engage in telescoping relation over said gripping tool, said gripping tool bearing against said grip bearing means to allow said gripping tool to rotate therewithin while substantially offsetting longitudinal forces applied to said drive shaft of said drive mechanism.

26. An autoclavable ligation instrument for use in dental or medical applications, comprising:
(a) a ligature gripping tool formed of an autoclavable material throughout, said gripping tool including a pair of opposed jaws which are movable between open and closed positions, and a handle member connected to each of said jaws for facilitating movement of said jaws between said open and closed positions;
(b) a readily releasable locking mechanism formed of an autoclavable material throughout and connected between said handle members of said ligature gripping tool for releasably locking said opposing jaws in said closed position;
(c) a multi-piece drive means including an elongated drive shaft having a longitudinal axis which extends between said jaws of said gripping tool, said drive means being formed of an autoclavable material throughout and connected to said ligature gripping tool for facilitating rotational movement of said gripping tool about an axis extending between said jaws thereof;
(d) a grip bearing means constructed for movable engagement of said gripping tool for offsetting longitudinal forces applied to said drive shaft during activation thereof; and
(e) said drive means being readily disassemblable to facilitate efficient autoclaving of said multiple pieces thereof.

27. The structure defined in claim 26, wherein said grip bearing means is generally tubular with a radially inwardly protruding annular bearing flange, said grip bearing means being telescoped over a portion of said gripping tool such that said bearing flange engages said gripping tool to offset longitudinal forces applied to said gripping tool while allowing rotational movement of said gripping tool therewithin.

* * * * *